United States Patent [19]
DeStefano et al.

[11] Patent Number: 5,829,696
[45] Date of Patent: Nov. 3, 1998

[54] SEALED GRINDING AND HOMOGENIZING APPARATUS

[75] Inventors: Michelle S. DeStefano, 201 Herman Dr., North Syracuse, N.Y. 13212; Michael H. Cynamon, 7 Pebble Hill Rd. North, DeWitt, N.Y. 13214; Donald W. Ziemendorf, Sanborn, N.Y.

[73] Assignees: Michelle S. DeStefano, N. Syracuse; Michael H. Cynamon, DeWitt, both of N.Y.

[21] Appl. No.: 921,222

[22] Filed: Aug. 27, 1997

[51] Int. Cl.[6] ........................................... B02C 19/00
[52] U.S. Cl. ..................... 241/169; 241/2; 241/169.1; 241/169.2; 241/199.12; 241/301
[58] Field of Search .................................. 241/2, 199.12, 241/199.11, 169.1, 169, 169.2, 301

[56] References Cited

U.S. PATENT DOCUMENTS

| | | | |
|---|---|---|---|
| 2,602,596 | 7/1952 | Jones et al. . | |
| 3,556,414 | 1/1971 | Eberly | 241/2 |
| 3,773,468 | 11/1973 | Hubbard et al. . | |
| 4,307,846 | 12/1981 | Spelsberg | 241/2 |
| 4,505,433 | 3/1985 | Selenke . | |
| 4,715,545 | 12/1987 | Hanifl et al. . | |
| 4,828,395 | 5/1989 | Saito et al. | 241/2 |
| 5,533,683 | 7/1996 | Fay et al. . | |

OTHER PUBLICATIONS

Ultem Design Guide (undated) pp. 3, 8–21.

*Primary Examiner*—Mark Rosenbaum
*Attorney, Agent, or Firm*—Trapani & Molldrem

[57] ABSTRACT

An apparatus for grinding specimens, comprises a container, a grinder, a closure for the container, and a seal contained in the closure. The container has an interior grinding surface and contains an opening through which specimens are introduced for grinding. The grinder has a grinding head and an actuator arm extending from the grinding head. The grinding head is adapted to engage the interior grinding surface of the container. Grinding is effected by moving the grinding head against the grinding surface, using the actuator arm. The closure is adapted to close the container and enclose the grinding head therein. The closure contains a passage through which the actuator arm extends when the closure is enclosing the grinding head. The seal is contained in the closure and coaxially aligned with the passage of the closure, such that the actuator arm slidably engages the seal when the arm passes through the closure.

16 Claims, 3 Drawing Sheets

SEALED GRINDING AND HOMOGENIZING APPARATUS

BACKGROUND OF THE INVENTION

1. Technical Field

The present invention relates generally to the field of laboratory testing and examination of biological specimens, and more particularly to apparatus for safely grinding and homogenizing such specimens in preparation for test and examination.

2. Background Art

In the past, the preparation of specimens of biological material for laboratory study (e.g., pathological or biochemical study) was accomplished by first collecting the biological material to be studied. The material was then transferred to an open mortar where it was comminuted or ground with a pestle. The ground sample was then transferred to a container and diluted with a solvent, such as saline solution, or with an oxygen reducing transport liquid. The diluted sample was then homogenized. The homogenized sample was transferred to a centrifuge machine for centrifugation, or to another station for some other type of processing or handling. This preparation process presented many opportunities for (1) contamination of the sample, (2) cross-contamination with other samples, and (3) harmful contamination of laboratory personnel.

The sample preparation process improved over the years with the advent of tissue grinders which included glass grinding tubes and piston-type Teflon® pestles. These devices improved the preparation process by consolidating several functions in one container—the grinding tube. The grinding tube for such devices serves as the container for collection, grinding, homogenizing, and processing. Such devices are currently on the market under the trademarks, Thomas®, Corning® and Wheaton®, and one such device is described in U.S. Pat. No. 3,773,468 to Hubbard et al. Even with the improvements offered by these devices, contamination has remained a serious problem—particularly, contamination due to aerosolization of biological material during the grinding step.

One early attempt to reduce the aerosolization problem is described in U.S. Pat. No. 4,505,433 to Selenke. Selenke describes a grinding container in which grinding and diluting occur simultaneously when a cap is screwed onto the container. The chance of aerosolization is reduced because the container is being closed during the grinding and dilution step. However, the utility of the Selenke device is limited to samples that do not require a thorough grinding—grinding occurs only during the twist of the cap. One potential drawback is that a technician may have a tendency to open and close the container repeated times to effect a more thorough grinding of the sample. If this is done, aerosolization is more likely and may even be promoted.

Another attempt to reduce aerosolization in a grinding apparatus was proposed in U.S. Pat. 4,715,545 to Hanifl et al. Hanifl describes a disposable tissue grinder employing a plastic sheath secured around the shaft of a grinder. The sheath is intended as a barrier to aerosols produced by the grinder. However, the interior surface of the sheath, which collects the aerosols, is in direct contact with the exterior surface of the grinding vessel. Thus, the grinding vessel can become a source of contamination after the grinder is removed from the vessel. In addition, there is a risk that the technician may reach inside the sheath and come in contact with aerosols on the interior surface of the sheath. Finally, due to the cost of these devices, laboratory personnel are reluctant to dispose of them after just one use. Thus, there is a tendency to reuse the devices, which could lead to harmful contamination of personnel and cross-contamination of samples.

A recent development in tissue grinding apparatus for reducing aerosolization is described in U.S. Pat. 5,533,683 to Fay et al. In Fay, a cap is thread onto a grinding vessel to seal the vessel during the grinding operation. The cap contains a hole through its center to receive the shaft of a pestle. The cap is made of a resilient material so that it conforms to the pestle shaft, but allows the shaft to rotate during grinding. A sealing flange may be integrally formed around the inner periphery of the hole to achieve a better sealing effect between the shaft and cap. One potential drawback with the Fay device is that the entire cap is flexible. Stresses imposed on the sealing flange and at the center of the cap, during grinding, may cause deformation and failure of the sealing function of the cap. If the sealing flange fails, the entire cap becomes useless. In addition, repeated autoclavings or other sterilization procedures may cause deformation and degradation of the flexible cap, and a resulting failure of the seal. Moreover, the Fay grinder requires a specially designed vessel and pestle; thus, existing stock of vessels and pestles in the laboratory cannot be utilized with the device.

OBJECTS AND SUMMARY OF THE INVENTION

It is therefore an object of the present invention to overcome the problems in the prior art, as discussed above, and to provide an improved grinding and homogenizing apparatus for biological specimens, such as tissue samples.

It is another object of the present invention to provide a grinding and homogenizing apparatus that minimizes (a) contamination of the specimen, (b) cross-contamination with other specimens, and (c) harmful contamination of laboratory personnel.

It is a further object of the present invention to provide a grinding and homogenizing apparatus that prevents the escape of aerosols while grinding and homogenizing a specimen.

It is still another object of the present invention to provide a grinding and homogenizing apparatus that accomplishes a thorough grinding of a specimen without increasing the risk of contamination by aerosols.

It is still a further object of the present invention to provide a grinding and homogenizing apparatus that reduces the risk of contamination when the pestle is removed from the grinding vessel.

It is yet another object of the present invention to provide a grinding and homogenizing apparatus that is resistant to deformation or degradation after repeated uses and sterilizations.

It is yet a further object of the present invention to provide a grinding and homogenizing apparatus employing a separate sealing component which can be replaced without having to replace the entire apparatus.

It is still yet another object of the present invention to provide a grinding and homogenizing apparatus that is reusable, even after many cleaning and sterilization operations.

It is still yet a further object of the present invention to provide a grinding and homogenizing apparatus that utilizes standard and readily available grinding tubes and pestles.

These and other objects are attained in accordance with the present invention wherein there is provided an apparatus for grinding and homogenizing a biological specimen for laboratory study. The apparatus comprises an elongated container, a grinder or pestle, a specially adapted closure for the container, and a seal which is removably contained in the closure.

The container has an interior grinding surface, and contains an opening through which the specimen is introduced for grinding. The grinder or pestle has a grinding head and an actuator arm extending from the grinding head. The grinding head is configured and dimensioned to fit through the opening and engage the interior grinding surface of the container. Grinding of the specimen is effected by moving the grinding head against the grinding surface of the container, using the actuator arm.

The closure is configured and dimensioned to close the opening of the container and enclose the grinding head therein for grinding. The closure contains a passage through which the actuator arm of the grinder extends when the grinding head is enclosed in the container. The seal is removably contained in the closure and is coaxially aligned with the passage of the closure. The actuator arm of the grinder slidably engages the seal when the arm passes through the closure. With the closure, seal and grinder in place, the container is substantially sealed during the grinding of the specimen.

The present invention may take the form of a subassembly for a grinding tube/pestle-type grinding apparatus. The subassembly includes a collar, a closure which mates with the collar, and a replaceable seal contained in the closure. The collar is adapted to slip over the tube and tightly engage a flange around the opening of the tube. The collar may include an o-ring which effects a seal between the flange and the collar. The collar includes a fitting which is in alignment with the opening of the tube when the tube and collar are engaged.

The closure includes a fitting which is adapted to mate tightly with the fitting of the collar, such that the opening of the tube is closed. The closure contains a hole which allows the actuator arm to extend through the closure when the grinding head is enclosed in the tube. The seal is removably contained in the closure, and is coaxially aligned with the hole in the closure. The actuator arm slidably engages the seal when the arm is made to move within the closure. The collar and closure are both made of an environmentally resistant material, such as Ultem® resin.

BRIEF DESCRIPTION OF THE DRAWING

Further objects of the present invention will become apparent from the following description of the preferred embodiment with reference to the accompanying drawing, in which.

DETAILED DESCRIPTION OF THE PREFERRED EMBODIMENT

Figure 1:
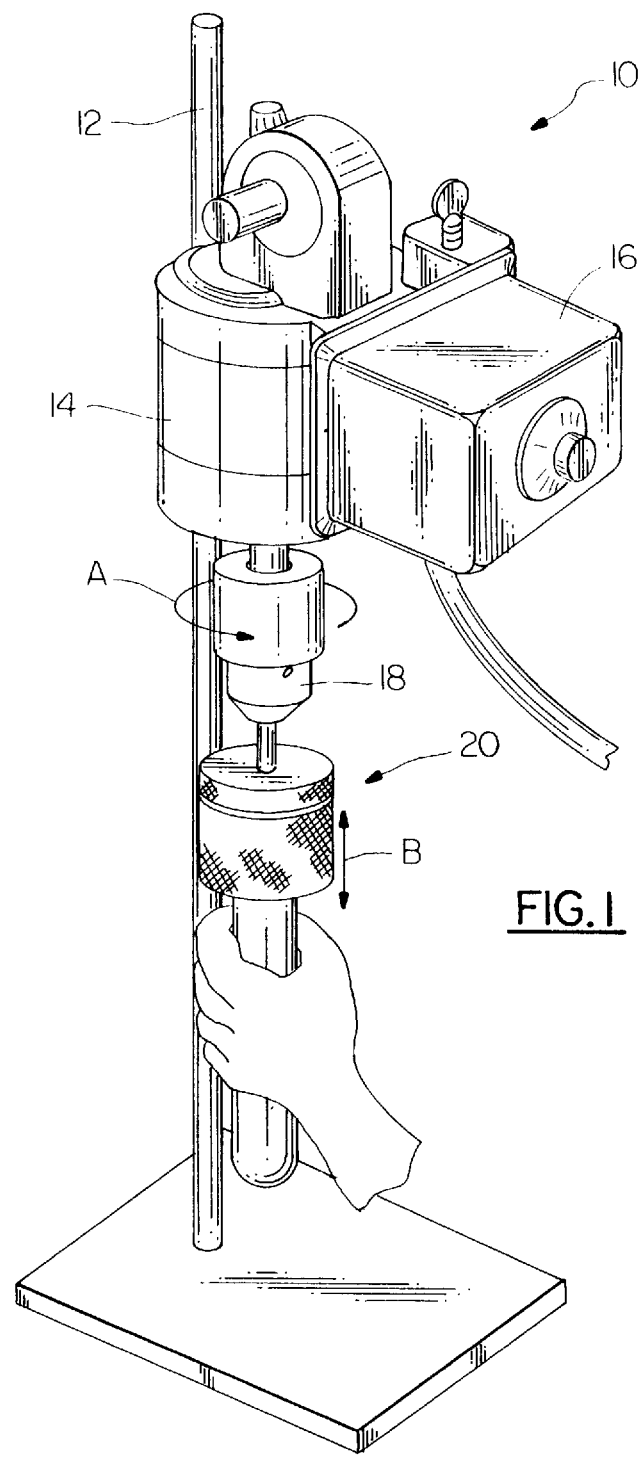
FIG. 1 is a perspective view of a grinding and homogenizing apparatus of the present invention being driven at a motorized grinding station.

With reference to FIG. 1, there is shown a motorized grinding station 10, including an upright bar stand 12, an electric motor 14 which is mounted to stand 12, a speed control unit 16 which is mounted to motor 14, and a chuck 18 which is coupled to the shaft of motor 14. A grinding apparatus 20, constructed in accordance with the present invention, is coupled to chuck 18 for grinding and homogenizing a biological specimen. A pestle or grinder (the shaft of which is coupled directly to chuck 18) is made to rotate inside apparatus 20, to effect the grinding operation. This rotational movement is represented in FIG. 1 by an arrow A. The operator grasps apparatus 20 with one hand to stabilize it during the grinding operation. The operator may move apparatus 20 up and down relative to the pestle, if necessary. This reciprocating movement is represented in FIG. 1 by arrow B. The operation of apparatus 20 will be described in greater detail hereinbelow.

Figure 2:
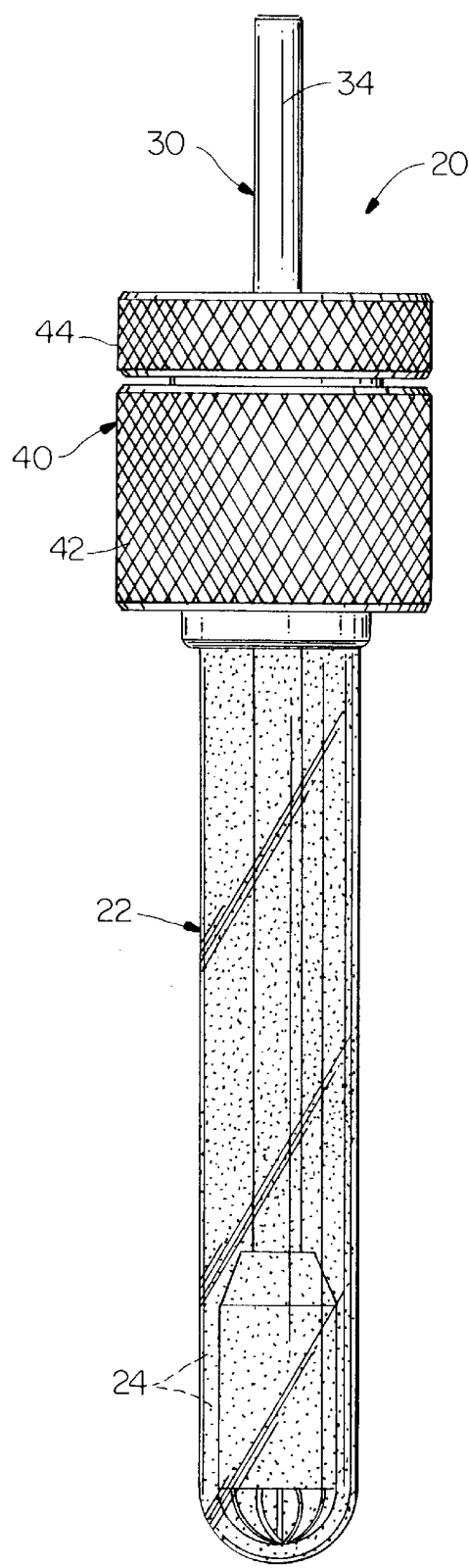
FIG. 2 is an enlarged elevation view of the grinding and homogenizing apparatus of the present invention.
Figure 3:
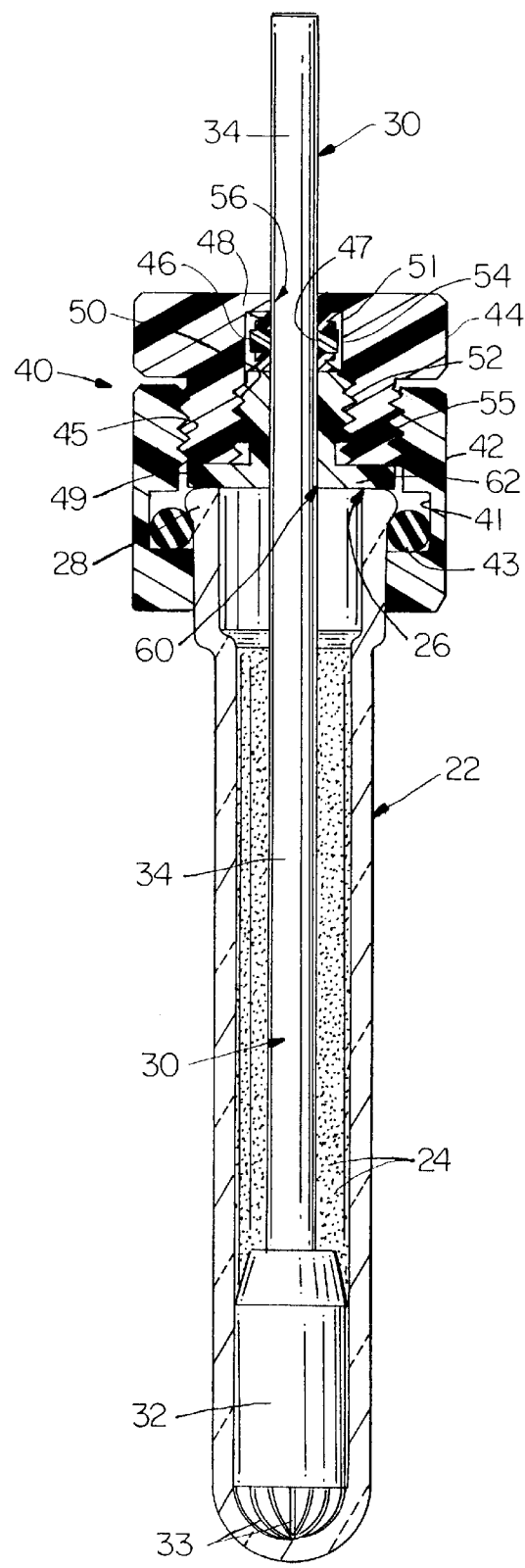
FIG. 3 is a cross-sectional view (except for the grinder) of the grinding and homogenizing apparatus of FIG. 2.
Figure 4:
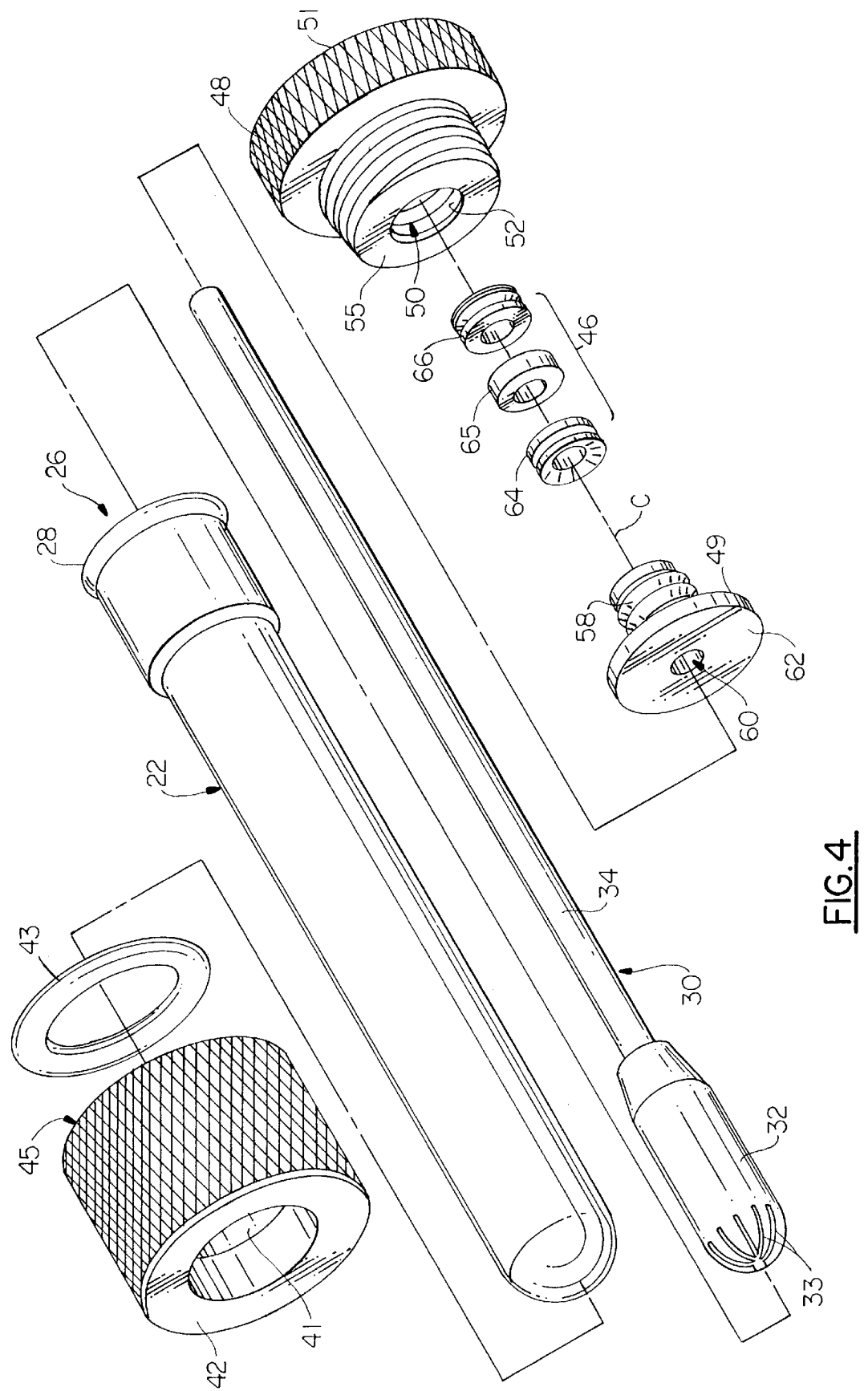
FIG. 4 is an exploded view of the grinding and homogenizing apparatus of FIG. 2.

Referring now to FIGS. 2–4, the construction of apparatus 20 will now be described in detail. Apparatus 20 comprises an elongated container 22, which is preferably a commercially available grinding tube made of borosilicate glass. One such tube is a Corning® Pyrex® tissue grinding tube. Tube 22 has a coarse, ground glass interior surface 24, suitable for grinding. The present invention, however, is not so limited; any type of coarse or serrated surface suitable for grinding (referred to herein as a grinding surface) is within the scope of the present invention. Tube 22 contains an opening 26 (See FIGS. 3 and 4) through which specimens are introduced to the tube for grinding. In the preferred form of tube, a flange or lip 28 surrounds opening 26. Flange 28 is a useful element in the assembly of the present invention, as will be described hereinbelow.

Apparatus 20 further includes a grinder or piston-type pestle 30 having a grinding head 32 and an actuator arm 34. Grinding head 32 is configured and dimensioned to fit through opening 26 of tube 22 and engage grinding surface 24. Grinding head 32 conforms closely with grinding surface 24—the clearance between surface 24 and head 32 is typically between 0.10 –0.15 mm. The surface of grinding head 32 may be abrasive, serrated or smooth, depending upon the particular specimen to be ground and the required fineness of the homogenized sample. In the embodiment shown in FIGS. 2–4, grinding head 32 is made of teflon and has a serrated outer surface 33.

Actuator arm 34 is made of stainless steel and is threaded into the rear end of grinding head 32. As best shown in FIG. 3, arm 34 extends from head 32 a sufficient distance to project out of the opening of tube 22 when head 32 is fully inserted into tube 22. Specimens are ground in tube 22 by manipulating actuator arm 34, and thus causing grinding head 32 to move against grinding surface 24. Actuator arm 34 is usually rotated to effect grinding of the specimen; however, arm 34 may be moved up and down for some grinding applications. As shown in FIG. 1, actuator arm 34 can be directly coupled to chuck 18 so that grinding head 32 can be power driven.

In the preferred embodiment, tube 22 and pestle 30 are standard commercially available items. One objective of the preferred embodiment is to use commercially available grinding tubes and pestles. This tends to minimize cost, allow personnel to work with familiar grinding equipment, and avoid the necessity of restocking new containers and grinders.

With further reference to FIGS. 2–4, there is shown a grinder subassembly 40 which includes a collar 42, a closure 44, and a seal assembly 46. As best shown in FIG. 3, collar 42 contains an o-ring groove 41 in which is seated an o-ring 43. o-ring 43 may be, for example, an ARP-319 Viton® o-ring. Collar 42 is configured and dimensioned to slip over the closed end of grinding tube 22, and slide up to and engage flange 28 (See FIG. 3). o-ring 43 establishes a compression fit for collar 42, around flange 28. This compression fit securely holds collar 42 on tube 22, and effects a water tight seal between collar 42 and flange 28. As shown in FIG. 3, collar 42 includes a threaded female fitting 45, which is in axial alignment with opening 26.

It is apparent from FIG. 3, that collar 42 will prevent the diluted sample (after grinding and homogenizing) from spilling over and running down the sides of tube 22, especially when the pestle is being removed from tube 22. Thus, the risk of harmful contamination to the technician, etc., is reduced. Collar 42 also functions as a protective wall to reduce the chance of contaminating the sample in tube 22.

As shown in FIG. 3, closure 44 contains a main passage 47 running through its center. In FIG. 4, the path of passage 47 is represented by a straight line segment C. Closure 44 comprises a cap 48 and a seal compressor 49. Cap 48 contains a hole 50 (See FIG. 4) which is greater in diameter and is coaxially aligned with main passage 47 (See FIG. 3). As shown in FIG. 3, hole 50 is defined by a threaded female fitting 52 and a seal chamber 54. Hole 50 terminates at an end wall 51 of cap 48 (See FIG. 3), and gives way to a smaller diameter hole 56 which extends through wall 51. Hole 56 is part of main passage 47. Closure 44 also includes a threaded male fitting 55 which is configured and dimensioned to thread tightly into female fitting 45 of collar 42.

Seal compressor 49 has a threaded male fitting 58 (See FIG. 4) which is configured and dimensioned to thread into fitting 52 of cap 48. Compressor 49 contains a hole 60 which extends through compressor 49. Hole 60 is part of main passage 47. As shown in FIG. 3, chamber 54 is defined by hole 50, between threaded fitting 58 (See FIG. 4) and wall 51 of cap 48. Compressor 49 has a sealing plate 62 which is dimensioned sufficiently to rest on flange 28 of tube 22 (See FIG. 3). When closure 44 is fully threaded into collar 42, plate 62 bears down onto flange 28 (and around opening 26) to effect a seal between closure 44 and tube 22 (See FIG. 3).

With further reference to FIGS. 3 and 4, the construction and operation of seal assembly 46 will now be described. Assembly 46 is referred to herein as a bi-directional ring seal. It includes a pair of oppositely disposed V-ring seals 64 and 66, separated by a rigid spacer ring 65 (See FIG. 4). Seals 64 and 66 mount directly on actuator arm 34 (See FIG. 3) and seal axially against compressor 49 (in the case of seal 64) and wall 51 (in the case of seal 66). Seals 64 and 66 are designed to maintain their sealing function even when the shaft is rotating or oscillating ("dynamic sealing"). Dynamic sealing is achieved because the flexible conical lip of each of seals 64 and 66 remains in contact with its respective counterface (compressor 49 and wall 51) during rotation or oscillation of actuator arm 34. Preferably, seals 64 and 66 are all-rubber Forsheda V-ring seals, made from DuPont Viton®, and commercially available from CR Industries in Sweden or CR Industries (Chicago Rawhide Mfg. Co.), Elgin, Ill.

Spacer ring 65 in assembly 46 functions to isolate seal 64 from seal 66 and ensure that the operation of one does not interfere with the operation of the other. Spacer ring 65 is made of a rigid material to provide seals 64 and 66 with a stable surface to ride on.

As shown in FIG. 3, assembly 46 is removably contained in chamber 54, and is coaxially aligned with passage 47. As shown in FIG. 3, fitting 58 of compressor 49 is carefully dimensioned so that, when it is fully threaded into cap 48, it acts against assembly 46 and compresses seals 64 and 66 against their respective counterfaces (i.e., fitting 58 and wall 51). This overall assembly ensures proper sealing from seals 64 and 66. Normally, seal assembly 46 is mounted to actuator arm 34 before assembly 46 is placed in chamber 54.

The preferred assembly procedure for grinding apparatus 20 is to first slip compressor 49 onto arm 34, in the orientation shown in FIG. 4. Then mount the components of assembly 46 on arm 34, in the order shown in FIG. 4. Cap 48 is then slipped onto arm 34, and assembly 46 is urged into and retained in chamber 54, when compressor 49 is threaded into cap 48. o-ring 43 is seated in o-ring groove 41 of collar 42. Grinding tube 22 is slipped through collar 42 until flange 28 engages o-ring 43 and creates a tight friction and sealing fit. Grinding head 32 is then inserted through opening 26 of tube 22, and pushed toward the closed end of tube 22. Closure 44 (which has already been assembled on arm 34) engages collar 42, and male fitting 55 of closure 44 threads tightly into female fitting 45 of collar 42.

With apparatus 20 fully assembled, opening 26 of tube 22 is now fully closed and sealed, and grinding head 32 is fully enclosed in tube 22 (See FIG. 3). Actuator arm 34 extends from grinding head 32 (inside tube 22) through passage 47 of closure 44 (to the outside tube 22). Arm 34 slidably engages seal assembly 46, as arm 34 is rotated or oscillated during a grinding operation. Seal assembly 46 functions to seal passage 47 when arm 34 is either static or in motion. Thus, tube 22 is sealed during grinding, and the escape of harmful aerosols is prevented.

One object of the preferred embodiment is for grinding apparatus 20 to be reusable. This objective is desirable because it costs less, in the long run, for reusable apparatus 20 than for disposable apparatus serving the same function. In order to achieve significant cost savings, apparatus 20 (or at least subassembly 40) should be reusable a fair number of times.

After each time apparatus 20 is used, its components must be sterilized before reuse. Sterilization normally requires soaking the components in a bleach solution for 30 minutes, washing them with soap, and autoclaving (steaming) them at 121 degrees Celsius and 40 psi for 30 minutes. The ability of the components of apparatus 20 to withstand repeated sterilizations has been a problem long-felt in the industry, and which is finally solved by the present invention. The problem is solved by manufacturing collar 42 and closure 44 from a material which is environmentally resistant, i.e., resistant to, for example: chemicals, such as bleach; soap solutions; solvents; long-term exposure to hot water; autoclaving; and UV radiation.

Collar 42 and closure 44 should also be resistant to deformation (i.e., rigid) resulting from stresses imposed on these components during grinding and sterilization. If these components undergo deformation, the sealing functions performed by these components may be significantly degraded or lost.

The preferred material for collar 42 and closure 44 is an amorphous thermoplastic polyetherimide resin, sold under the registered trademark, Ultem®, and manufactured and sold by General Electric. This material is both environmentally resistant and extremely resistant to deformation or deflection. This material is suitable whether the components are to be manufactured by way of machining or injection molding. If machining the components, Ultem® 1000 is suitable for the purposes of the present invention. It is anticipated that collar 42 and closure 44, made from Ultem®, can be reused about 100 times before replacement is required.

As best shown in FIGS. 2 and 4, the outer cylindrical surfaces of collar 42 and cap 48 are knurled to facilitate the gripping of these components during assembly.

With respect to seal assembly 46, Ultem® 1000 is the preferred material for spacer ring 65. Seals 64 and 66 are made of DuPont Viton® material. Seals 64 and 66 usually need to be replaced after about 10 uses. One aspect of the present invention is that the seal assembly is separate from the closure of the grinding tube. This feature permits the closure to be made of a rigid material, which can withstand mechanical and environmental stresses, while offering an effective dynamic seal between the closure and the actuator arm. If the seal fails, it can be easily and economically replaced without having to discard the closure (which may be more expensive than the seal).

A typical application of apparatus 20 is to grind and homogenize a mouse organ (e.g., a spleen) for pathological study. Grinding tube 22 is filled with a given volume of saline solution (e.g., 0.5 –1.0 ml) and the organ is placed in the solution for grinding and homogenizing. Grinding tube 22 is closed and sealed using subassembly 40. Actuator arm 34 is attached to chuck 18, and the tube is held by the operator (See FIG. 1). Motor 14 is started, and its speed is adjusted to a desired rate for grinding and homogenizing by using unit 16. Once the organ is ground to a fine homogenate, motor 14 is stopped and closure 44 is unscrewed from collar 42. A volume of the organ tissue homogenate is then either diluted for further processing or plated for examination.

While the preferred embodiments of the invention have been particularly described in the specification and illustrated in the drawing, it should be understood that the invention is not so limited. Many modifications, equivalents, and adaptations of the invention will become apparent to those skilled in the art without departing from the spirit and scope of the invention as defined in the appended claims.

What is claimed is:

1. An apparatus for grinding a specimen, such as a tissue sample, said apparatus comprising:
   an elongated container, having an interior grinding surface and containing an opening through which the specimen is introduced for grinding;
   a grinder, having a grinding head and an actuator arm extending from the grinding head, the grinding head being configured and dimensioned to fit through the opening and engage the interior grinding surface of said container, the grinding of the specimen being effected by moving the grinding head against the grinding surface of said container using the actuator arm;
   a closure, made of an environmentally resistant material, and being configured and dimensioned to close the opening of said container and enclose the grinding head therein during the grinding of the specimen, said closure containing a passage through which the actuator arm extends when the grinding head is enclosed by said closure; and
   a seal, removably contained in said closure, and being coaxially aligned with the passage of said closure, such that the actuator arm of said grinder slidably engages said seal when the arm passes through said closure,
   whereby said container is substantially sealed during the grinding of the specimen.

2. The apparatus as recited in claim 1, wherein said seal is a bi-directional ring seal.

3. The apparatus as recited in claim 2, wherein said bi-directional ring seal includes a pair of opposing ring seals separated by a spacer ring.

4. The apparatus as recited in claim 1, wherein said closure includes a sealing plate configured and dimensioned to bear down around the opening of said container and effect a seal between said closure and said container.

5. The apparatus as recited in claim 1, wherein said closure contains a seal chamber coaxially aligned with the passage of said closure, said seal being retained in the chamber in coaxial alignment with the passage.

6. The apparatus as recited in claim 5, wherein said closure includes a cap portion and a sealing portion,
   said cap portion containing a hole which is coaxially aligned with the passage of said closure,
   said sealing portion having a male fitting configured and dimensioned to engage tightly into the hole in said cap portion,
   said sealing portion containing a hole therethrough which defines a portion of the passage of said closure,
   the seal chamber of said closure being defined by the hole in said cap portion, between the male fitting of said sealing portion and the cap portion, when said sealing portion is engaged in said cap portion.

7. The apparatus as recited in claim 6, wherein the sealing portion of said closure has a sealing plate configured and dimensioned to bear down around the opening of said container and effect a seal between said closure and said container.

8. The apparatus as recited in claim 1, wherein said container includes a collar around the container opening, said collar defining a female fitting; and wherein said closure includes a male fitting configured and dimensioned to engage tightly into the female fitting of said collar, whereby a closure of the opening of said container is effected.

9. The apparatus as recited in claim 8, wherein said container includes an elongated tube containing an opening which constitutes the opening of said container, said tube having a flange around the opening, said collar tightly engaging the flange of said tube to effect a seal between the flange and said collar.

10. The apparatus as recited in claim 9, further comprising an o-ring seated between the flange and said collar to effect a water tight seal therebetween.

11. The apparatus as recited in claim 1, wherein said closure is made of an Ultem® resin.

12. A subassembly for a grinding apparatus, wherein the grinding apparatus is of the type which includes an elongated tube containing an opening and having a flange around the opening, and which includes a grinder having a grinding head and an actuator arm extending from the grinding head, and the grinding head being adapted to fit through the opening of the tube and be manipulated therein by working the actuator arm, said subassembly comprising:
   a collar, configured and dimensioned to slip over the tube and tightly engage the flange of the tube, so that a seal is effected between the flange and said collar, said collar including a fitting which is in alignment with the opening of the tube when said collar engages the tube;
   a closure, including a fitting which is configured and dimensioned to mate tightly with the fitting of said collar and close the opening of the tube, said closure containing a passage dimensioned to allow the actuator arm of the grinder to extend therethrough when the grinding head is inside the tube and said closure is mated with said collar; and
   a seal, removably contained in said closure and coaxially aligned with the hole in said closure such that the actuator arm of the grinder slidably engages said seal when the arm is made to pass through said closure; and wherein said collar and said closure are made of an environmentally resistant material.

13. The subassembly as recited in claim 12, further comprising an o-ring seated inside said collar, and being positioned, configured and dimensioned to effect a water tight seal between said collar and the flange of the tube.

14. The subassembly as recited in claim 12, wherein said seal is a bi-directional ring seal having a pair of opposing ring seals separated by a spacer ring.

15. The subassembly as recited in claim 12, wherein said closure includes a sealing plate configured and dimensioned to bear down around the opening of the tube and effect a seal between said closure and the tube.

16. The subassembly as recited in claim 12, wherein said collar and said closure are made of an Ultem® resin.

* * * * *